US009931175B2

(12) United States Patent
Bischoff et al.

(10) Patent No.: US 9,931,175 B2
(45) Date of Patent: Apr. 3, 2018

(54) CONTAINER WITH COVER (71) Applicant: Mauser-Werke GmbH, Brühl (DE)

(72) Inventors: Sebastian Bischoff, Bonn (DE); Daniel Siede, Pulheim (DE)

(73) Assignee: MAUSER-WERKE GMBH, Brühl (DE)

(*) Notice: Subject to any disclaimer, the term of this patent is extended or adjusted under 35 U.S.C. 154(b) by 0 days.

(21) Appl. No.: 15/511,142

(22) PCT Filed: Sep. 15, 2015

(86) PCT No.: PCT/EP2015/001841
§ 371 (c)(1),
(2) Date: Mar. 14, 2017

(87) PCT Pub. No.: WO2016/041632
PCT Pub. Date: Mar. 24, 2016

(65) Prior Publication Data
US 2017/0273753 A1 Sep. 28, 2017

(30) Foreign Application Priority Data
Sep. 15, 2014 (DE) ........................ 10 2014 013 330

(51) Int. Cl.
B65D 41/16 (2006.01)
A61B 50/30 (2016.01)
(Continued)

(52) U.S. Cl.
CPC ............ *A61B 50/30* (2016.02); *B65F 1/1615* (2013.01); *A61B 2050/005* (2016.02);
(Continued)

(58) Field of Classification Search
CPC .... A61B 50/30; B65D 5/6611; B65D 5/6647; B65D 5/6673; B65D 50/068;
(Continued)

(56) References Cited

U.S. PATENT DOCUMENTS 4,585,138 A * 4/1986 Jonkers .............. B65D 43/0212
220/614
4,742,935 A 5/1988 Schellenberg
(Continued)

FOREIGN PATENT DOCUMENTS

EP 0 168 877 1/1986
EP 0 256 253 2/1988
(Continued)

OTHER PUBLICATIONS

International Search Report issued by the European Patent Office in International Application PCT/EP2015/001841 dated Nov. 17, 2015.

*Primary Examiner* — Shawn M Braden
(74) *Attorney, Agent, or Firm* — Henry M. Feiereisen LLC (57) ABSTRACT A container includes a base, and a jacket adjoining the base and having a peripheral flange which defines an opening cross section which can be closed by a cover. The cover includes first snap-fit hooks distributed about a periphery of the cover for engagement in complementing first latching openings in the peripheral flange to thereby establish a form fit that prevents a movement away from the base and parallel to a vertical axis of the container in perpendicular relation to the base. The peripheral flange has four corner regions, each provided with a second latching opening for engagement of a second snap-fit hook of the cover. The second latching opening has at least one portion configured curved or inclined in relation to both a transverse axis and a longitudinal axis of the container, or has at least two straight portions extending at an inclination in relation to one another.

14 Claims, 5 Drawing Sheets (51) Int. Cl.
*B65F 1/16* (2006.01)
*A61B 50/00* (2016.01)
*B65D 43/14* (2006.01)
*B65F 1/02* (2006.01)

(52) U.S. Cl.
CPC ...... *A61B 2050/0083* (2016.02); *B65D 43/14* (2013.01); *B65F 1/02* (2013.01)

(58) Field of Classification Search
CPC .... B65D 55/0863; B65D 45/30; B65D 55/06; B65D 2543/00101; B65D 43/22; B65D 41/16; B65D 42/0204; B65D 43/0252; B65D 43/0241; B65D 43/0256
USPC ............... 220/274, 780, 621, 258.2, 265
See application file for complete search history.

(56) References Cited

U.S. PATENT DOCUMENTS

| | | | | |
|---|---|---|---|---|
| 5,979,691 | A * | 11/1999 | Von Holdt | B65D 43/0256 220/266 |
| 6,851,569 | B2 * | 2/2005 | Conti | B65D 21/0219 215/216 |
| 9,233,777 | B2 | 1/2016 | Weyrauch et al. | |

FOREIGN PATENT DOCUMENTS

| | | |
|---|---|---|
| EP | 0 610 904 | 8/1994 |
| EP | 1 790 590 | 5/2007 |
| NL | 1023835 | 1/2005 |
| WO | WO 2007/139377 | 12/2007 |

\* cited by examiner

CONTAINER WITH COVER

CROSS-REFERENCES TO RELATED APPLICATIONS

This application is the U.S. National Stage of International Application No. PCT/EP2015/001841, filed Sep. 15, 2015, which designated the United States and has been published as International Publication No. WO 2016/041632 A1 which claims the priority of German Patent Application, Serial No. DE 10 2014 013 330.3, filed Sep. 15, 2014, pursuant to 35 U.S.C. 119(a)-(d).

INTRODUCTION

The invention relates to a container having
a base;
a vertical axis which runs so as to be perpendicular to the base;
a jacket which adjoins the base in an encircling manner and which at one end that faces away from the base has an encircling and outwardly projecting peripheral flange;
an opening cross section which is defined by that end of the jacket that faces away from the base and which permits access to the respective internal volume of the container; and
a cover which in the closing position thereof closes the opening cross section and which on peripheries is provided in an encircling manner with snap-fit hooks which are disposed so as to be distributed and each mutually spaced from the other, and which when viewed in a plane of the peripheral flange are preferably elongate;
wherein the snap-fit hooks in the closing position of the cover engage in preferably elongate latching openings in the peripheral flange, which are adapted to said snap-fit hooks, on account of which a form fit which prevents movement which is directed away from the base and parallel with the vertical axis of the container is formed, and wherein the cover in the closing position tightly closes the internal volume of the container.

PRIOR ART

Containers are employed in a versatile manner and in particular serve for storing, transporting, collecting, and disposing of substances or materials, containers being known in a wide range of sizes and shapes. Waste containers which are provided for employment in hospitals, veterinary clinics, medical and dental practices, and in medical research and development laboratories, where in particular infectious waste arises, are used only once or are disposed of together with the waste located therein, respectively, once said containers have been tightly closed in a suitable manner. For closing, snap-fit hooks which are located on the cover are typically introduced into latching openings on the container that are provided therefor, wherein during latching the snap-fit hooks modify their position in relation to the position during introduction such that said snap-fit hooks are no longer removable from the latching opening without being manipulated.

A container of this type with a cover and the features mentioned at the outset is known, for example, from EP 0 168 877 B1, the cover here being fixed to the container such that the snap-fit hooks, which are configured in a lug-type manner having an end-side hook portion and thus have a certain elasticity in the transverse direction thereof, are introduced into the latching openings. If the container has been closed with the cover, the snap-fit hooks engage in the latching openings such that the hook portions of the snap-fit hooks each encompass one wall of the latching openings. Thus, subsequent removal of the cover is barely possible by virtue of the multiplicity of snap-fit hooks which engage on the circumference of the peripheral flange. The cover may only be removed by simultaneously depressing all snap-fit hooks such that the hook portions make their way into the plane of the latching openings while the cover is simultaneously lifted, this being extremely difficult even with a plurality of persons acting conjointly. However, subsequent opening of a container which is closed with the cover is not at all desired by virtue of the fact that the containers serve for storing and dispatching sensitive waste. Rather, a durable closure of the container and a simultaneous tight seat of the cover are required, this requiring intense engagement of the snap-fit hooks in the latching openings.

Unfortunately, however, it does happen to an unsatisfactory extent that individual snap-fit hooks or a plurality thereof, in particular snap-fit hooks in the same row, during positioning of the cover slide along the internal side of the jacket instead of engaging in the latching openings in the peripheral flange that are provided therefor, this being caused in that the cover may only be pressed onto the container with great difficulty in order for said cover to be horizontally aligned and for all snap-fit hooks to simultaneously slide into the latching openings. This is difficult because during the closing procedure, on account of friction forces which are created and of slight flexing of the snap-fit hooks, said snap-fit hooks generate resistance which increases with the number of snap-fit hooks that are intended to simultaneously latch. For this reason, the containers are typically closed with a cover such that the cover is initially attached to one side, in order for the snap-fit hooks to be introduced here. The cover, which is thus obliquely aligned and is already latched in one region, is then successively further fixed to the container in that the snap-fit hooks are successively pushed into the latching openings provided therefor, wherein said snap-fit hooks are often briefly bent in a direction which is transverse to the vertical axis, or wherein a slight rotation of the cover about the vertical axis thereof which is at times not noticeable to the user is performed, respectively. This is possible since the lug-type snap-fit cams, on account of the length thereof, may be slightly resilient in the above-mentioned direction.

Here, it may arise that certain snap-fit hooks permanently bear on the inner jacket face (and thus do not develop any effect), whereas other snap-fit hooks latch in an orderly manner such that the leak-tightness of the closed container is not guaranteed, this being unacceptable with a view in particular to escaping odors or to liquids which leak when the container is being disposed of. This is particularly valid since transportation of potentially infectious and contaminous medical waste by transport law is only permitted in completely closed containers. Removal of the cover in order for the cover to be repositioned is not possible because of the prescribed quasi-irreversible latching of the remaining snap-fit hooks of the cover.

Object

With a view to the abovementioned disadvantages of the known containers, it is an object of the present invention to refine a container having the features mentioned at the outset in such a manner that orderly engagement of all snap-fit hooks in the latching openings provided therefor is guaranteed.

Achievement

The aforementioned object is achieved by a container of the type mentioned at the outset which is furthermore distinguished in that at least one latching opening is disposed in each of four corner regions of the peripheral flange, wherein these latching openings when viewed in the plane of the peripheral flange at least in portions run so as to be curved or inclined in relation to both a transverse axis and a longitudinal axis of the container, or are assembled from at least two straight portions which run so as to be mutually inclined, and in that the associated snap-fit hooks are configured so as to be adapted thereto.

This profile according to the invention of the latching openings, which hereunder will be collectively referred to as "nonlinear", ensures that the associated snap-fit hooks cannot make their way into the latching openings when the former to this end would have to be deformed in the form of a rotation about the vertical axis, the latter being almost impossible in the case of normal force being employed by the user. While conventional snap-fit hooks which run parallel with the transverse axis or the longitudinal axis have a certain inherent tolerance when being incorporated into a latching opening (lateral deflections which are transverse to the longitudinal direction of the assigned latching opening are easily possible, in particular), the snap-fit hook which runs in a non-linear manner, when being introduced in an orderly manner, may only be incorporated into the latching opening provided by the cover when aligned in an orderly manner, that is to say when the cover is also aligned in an overall orderly manner. In particular, an attempt at introducing the non-linear snap-fit hook so as to be somewhat offset in the transverse direction or the longitudinal direction would be unsuccessful since said non-linear snap-fit hook would then collide with the upper end of the jacket.

Moreover, the latching opening which is shaped according to the invention has the effect that the cover, upon introduction of the associated snap-fit hook into the latching opening which is curved, inclined, or assembled from two portions, may no longer be displaced in the direction of the longitudinal axis or transverse axis, such that it is achieved that the remaining snap-fit hooks may make their way exclusively into the corresponding latching openings. The at least one "non-linear" snap-fit hook, or the plurality thereof, thus assumes or assume, respectively, a guiding function for the orderly alignment and insertion of the remaining snap-fit hooks which are disposed so as to be parallel with the longitudinal or transverse axis and are preferably each disposed behind one another in a linear manner, said snap-fit hooks being individually present in the prior art. Faulty closing of the cover, such as may arise in the case of containers in the prior art, is thus excluded (to the greatest possible extent).

A curved latching opening according to the invention, and a corresponding snap-fit hook, may therefore be formed as an arcuate portion without a reversal point, or else have a curve-type profile with a reversal point or reversal points, such as an S-shaped profile, for example. In the case of a latching opening according to the invention, or in the case of a snap-fit hook according to the invention having a straight profile, respectively, it is only to be noted that the straight line has a direction which is not identical to that of the transverse axis or the longitudinal axis of the container.

Moreover, however, it is also conceivable for the at least one latching opening and the associated snap-fit hook to be assembled from straight portions which run in a mutually inclined manner, wherein two portions may configure a corner with an arbitrary angle, for example, or else a plurality of straight portions may configure part of a polygon.

In one advantageous design embodiment of the container according to the invention, the jacket has in mutually parallel sectional planes which each run so as to be perpendicular to the vertical axis of the container in each case the shape of a rounded rectangle, wherein also the peripheral flange preferably has the shape of a rounded rectangle and a plurality of latching openings are disposed in portions of the peripheral flange that are mutually opposite in pairs and run in a straight line, and at least one latching opening is disposed in each of all four arcuate portions of the peripheral flange, wherein the arcuate portions each interconnect two straight portions which are disposed so as to be mutually orthogonal. It is therefore convenient, for the latching opening according to the invention and for the associated snap-fit hook, to acquire the geometry of the arcuate portion such that the latching opening and the snap-fit hook run parallel with a longitudinal axis of the arcuate portion. However, it is likewise conceivable for a straight-line latching opening or another latching opening which is configured as has been described above to be provided in the arcuate portion of the peripheral flange, the associated snap-fit hook here having to be configured in an analogous manner.

Advantageously, the snap-fit hooks are each assembled from a lug-type tongue portion which faces the cover and from a hook portion in each case adjoining an end of the tongue portion that faces away from the cover, wherein the tongue portions are preferably elastically deformable in a direction which is perpendicular to the vertical axis of the container.

With a view to easy placement of the cover it is of particular advantage for the latching openings each to have on that side thereof that faces the vertical axis of the container a spacing from the jacket that is smaller than 5 mm, preferably smaller than 2 mm, further preferably smaller than 1 mm, even further preferably equal to zero. The smaller the spacing of the latching openings from the jacket, the more comfortably the snap-fit hooks of the cover may be introduced into the latching openings.

When an end of the container that faces away from the base is formed by an encircling sealing web which preferably forms an extension of an encircling container wall which defines the jacket, wherein the sealing web in the closing position of the container bears in a sealing manner on a seal which is located in an encircling sealing groove in the cover that is adapted to the sealing web, wherein an end portion of the sealing web preferably extends into the sealing groove, the closed container is distinguished by the leak-tightness thereof which is inter alia also advantageous with a view to odors which are created in the container. Here, it is of particular advantage for the encircling sealing web to bear on the seal in the sealing groove even when the container is lifted using a handle provided on the cover, and relative displacement between the cover and the container may thus arise without the tightness of the connection being compromised.

It should finally be noted that the various features of the dependent claims may each be implemented individually or in arbitrary combinations of a plurality thereof in variants of the invention.

EXEMPLARY EMBODIMENT

The invention described above will be discussed in more detail hereunder by means of exemplary embodiments which are illustrated in the figures in which.

Figure 1A:
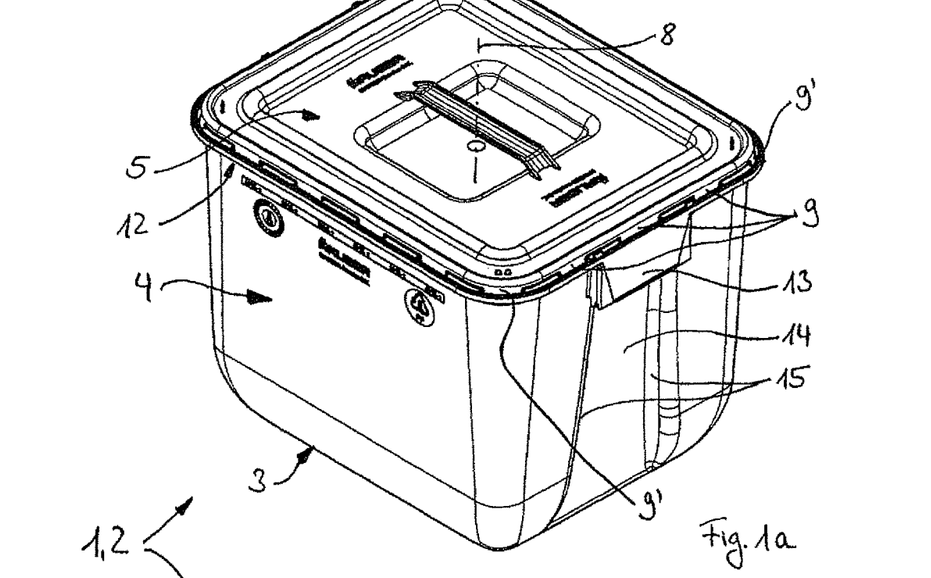
FIGS. 1a and 1b show three-dimensional views of a container according to the invention.
Figure 1B:
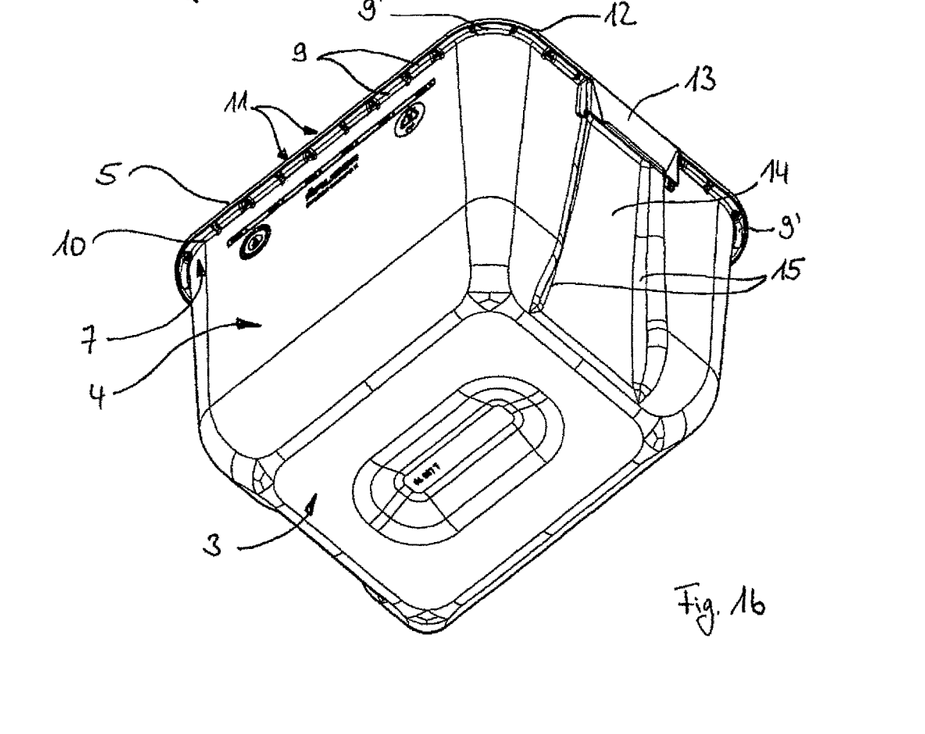

An embodiment for a container 1 according to the invention is illustrated in FIGS. 1a and 1b which show a three-dimensional view of the container 1 in the closing position 2 thereof from above and from below, respectively. The container 1 is assembled from a base 3, a jacket 4 which adjoins thereto in an encircling manner, and a cover 5, wherein the cover 5 closes an opening cross section 6 (cf. FIG. 3) to an interior volume of the container 1 that is defined by an end 7 of the jacket 4 that faces away from the base 3. A vertical axis 8 of the container 1 is congruent with the vertical snap-fit hooks 9, 9' which are distributed in an encircling manner, each being disposed so as to be mutually spaced from the other, on peripheries 10 of the cover 5, in the shown closing position 2 of the container 1 engage in corresponding latching openings 11, 11' of an encircling and outwardly projecting peripheral flange 12 of the jacket 4. The arrangement and the geometry of the peripheral flange 12 with its latching openings 11, 11' and of the snap-fit hooks 9, 9' of the cover 5 will be clarified in more detail in the following figures.

On each of mutually opposite short sides, the container 1 is equipped with a carrying lug 13 on an upper side. In order to enable comfortable engagement in the carrying lugs 13, and in order to enhance the stability of the container 1 in the region of the carrying lugs 13, said container 1 has on the short lateral faces thereof a vertically running inward bulge 14, the width of which on the upper side of the container 1 approximately corresponds to a length of the carrying lug 13, whereas the width of said inward bulge 14 on the base 3 of the container 1 is larger. Consequently, two mutually opposite ribs 15 of the inward bulge 14 run so as to be mutually oblique.

Figure 2A:
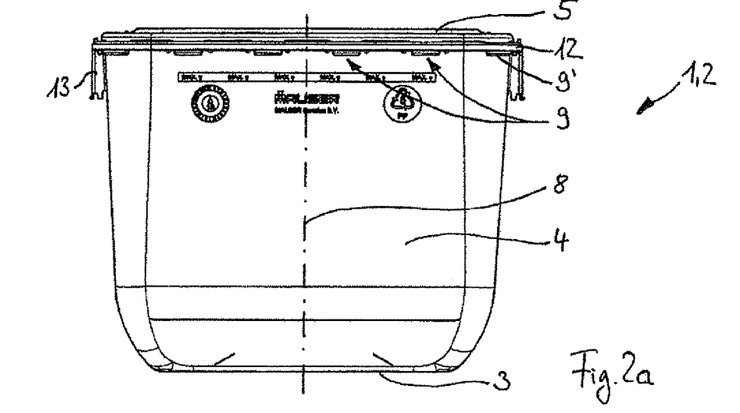
FIGS. 2a to 2c show a front view, a view from below, and a plan view of the container from FIG. 1.
Figure 2B:
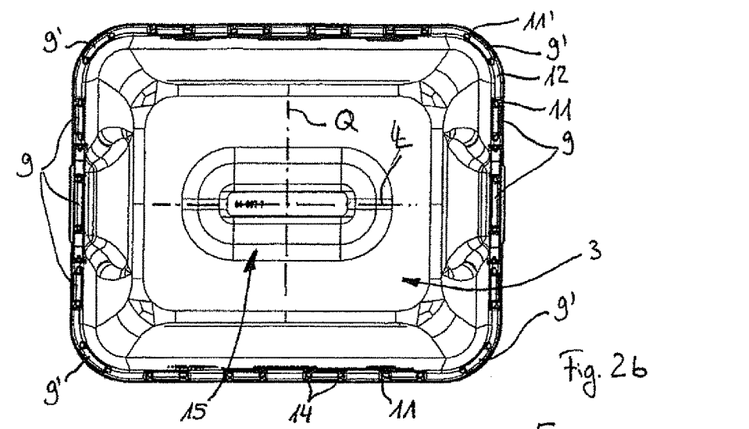
Figure 2C:
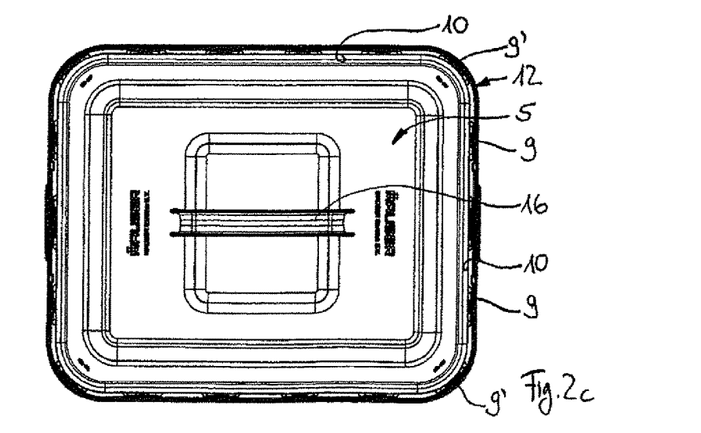

The jacket 4 of the container 1 with its peripheral flange 12 and also the cover 5 each have in all horizontal sections the shape of a rounded rectangle, this also being readily identifiable from FIGS. 2a to 2c.

FIG. 2a shows a front view of the container 1 onto a long lateral face thereof, from which it becomes clear that the vertical axis 8 runs so as to be perpendicular to the base 3 of the container 1. The peripheral flange 12, in latching openings 11, 11' which are not identifiable in FIG. 2a, is penetrated by the snap-fit hooks 9, 9' of the cover 5 such that irreversible tight closing of the container 1 is achieved.

The peripheral flange 12 with its latching openings 11, 11' which are distributed in an encircling manner, each being disposed so as to be mutually spaced from the other, can be seen from FIG. 2b which shows a view of the container 1 from below, the engaging snap-fit hooks 9, 9' being located in each case in the latching openings 11, 11'. When viewed in the longitudinal direction of the latching openings 11, 11' and of the snap-fit hooks 9, 9', said longitudinal direction running in each case in the circumferential direction of the peripheral flange 12, the latching openings 11, 11 have a larger length than the snap-fit hooks 9, 9' such that small intermediate spaces 14 in relation to transverse walls of the latching openings 11, 11' remain beside the snap-fit hooks 9, 9' in both directions. The latching openings 11, 11' are differentiated into latching openings 11 which are configured so as to be straight, and latching openings 11' which are configured so as to be arcuate. In an analogous manner thereto, there are snap-fit hooks 9 which run in a straight manner, and arcuate snap-fit hooks 9', the arcuate latching openings 11' and snap-fit hooks 9' being located in the four rounded corners of the peripheral flange 12 and of the cover 5. The latching openings 11' and the snap-fit hooks 9' overall thus run in a curved manner and so as to be inclined to a transverse axis Q and a longitudinal axis L of the container 1.

It can likewise be derived from FIG. 2b that the base 3 of the container 1 has a centrally disposed depression 15 which in terms of the dimensions thereof is adapted to a handle 16 on the cover 5 which is to be seen in FIG. 2c.

The peripheral flange 12, the peripheries 10 of the cover 5, the snap-fit hooks 9, 9', and the latching openings 11, 11' may also be derived from FIG. 2c which shows a plan view of the container 1 which is closed with the cover 5. Moreover, the handle 16 is shown in a central region of the cover 5.

Figure 3:
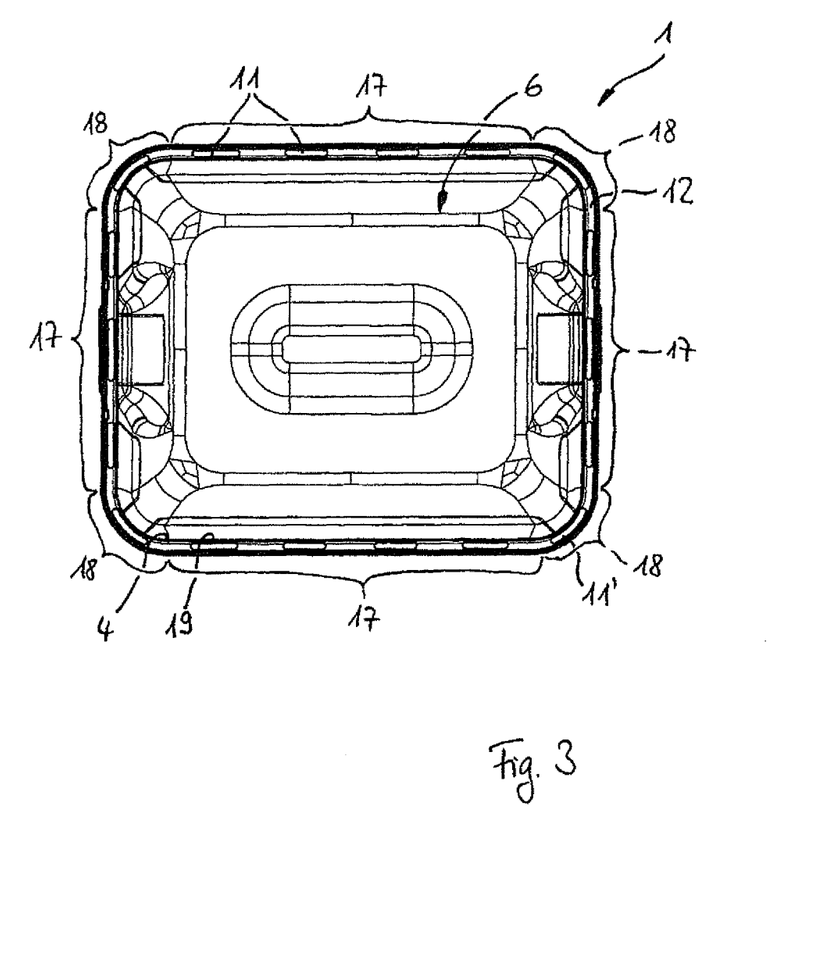
FIG. 3 shows a plan view of the container from FIG. 1, without a cover.

In order to be able to explore the geometry of the latching openings 11, 11' in more detail, FIG. 3 shows a plan view of the container 1 without the cover 5. Firstly, the peripheral flange 12 has on portions 17 which run in a straight manner a plurality of latching openings 11 which are mutually opposite in pairs and which are configured in an elongate manner and likewise have a straight profile. Four latching openings 11 are in each case provided along the long portions 17 of the peripheral flange 12, and only three latching openings 11 are in each case provided along the short portions 17. The peripheral flange 12, by virtue of the shape thereof as a rounded rectangle, furthermore comprises four arcuate portions 18 which each interconnect two straight portions 17 which run so as to be mutually perpendicular, that is to say each connect a short straight portion to a long straight portion 17. One latching opening 11' is also located in each of the arcuate portions 18, which latching openings 11' run in an arcuate manner analogous to the curvature of the arcuate portion 18. A side 19 of the latching openings 11, 11' that faces the vertical axis 8 does not have any spacing from the jacket 4 in any case, meaning that the side 19 of the latching openings 11, 11' that faces the vertical axis 8 is flush with the jacket 4.

Figures 4A, 4B, 4C, 4D, 4E, 4F:
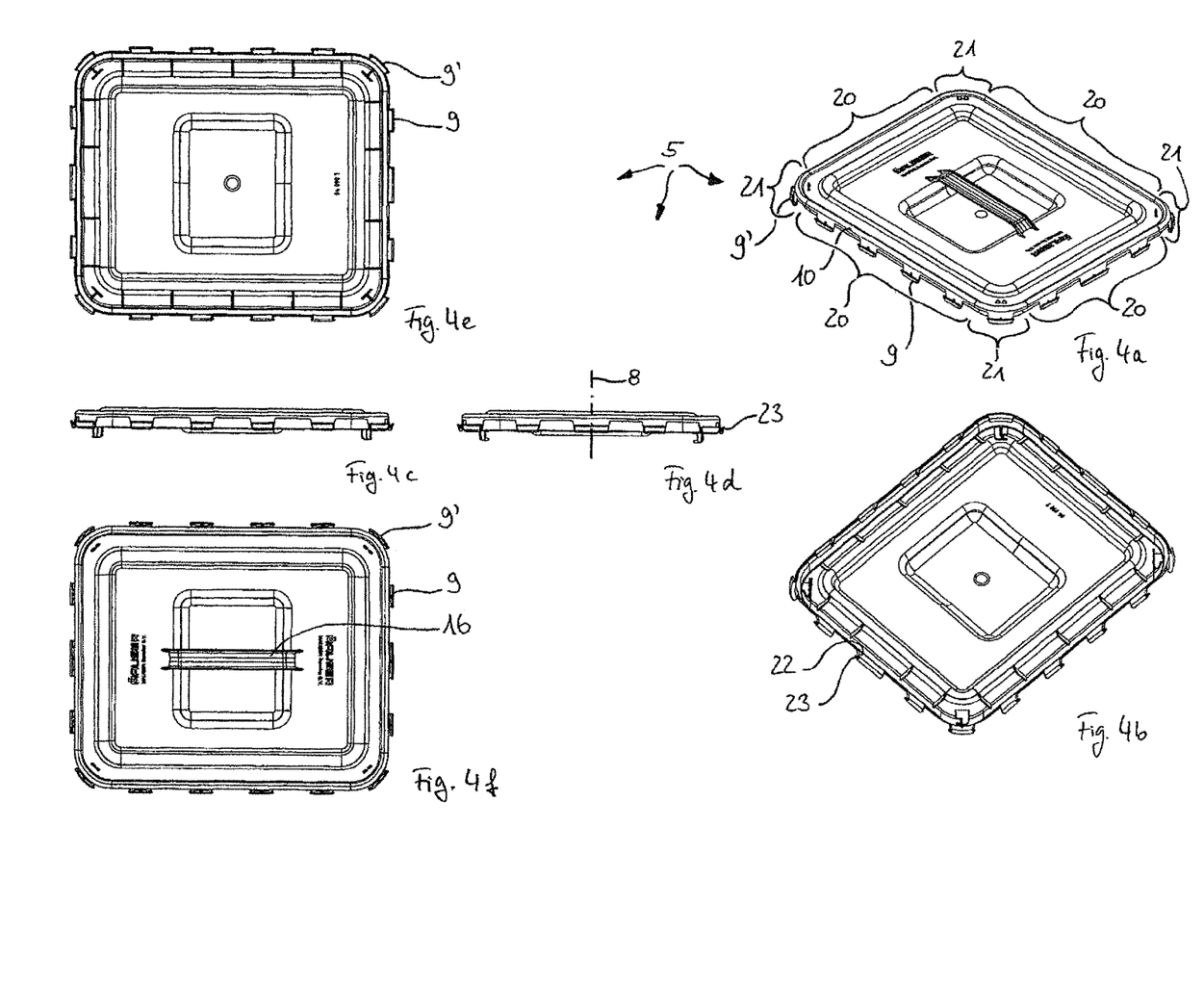
FIGS. 4a to 4f show three-dimensional and two-dimensional views of the cover from FIG. 1.

FIGS. 4a to 4f merely depict the cover 5 from various perspectives, FIG. 4a being a three-dimensional plan view, FIG. 4b being a three-dimensional view from below, FIG. 4c being a front view, FIG. 4d being a side view, FIG. 4e being a view from below, and FIG. 4f being a plan view of the cover 5. The cover 5 has in sectional planes which are perpendicular to the vertical axis 8 of the container in each case the shape of a rounded rectangle such that an encircling periphery 10 of the cover 5 is also assembled from four straight portions 20 and four arcuate portions 21. Four snap-fit hooks 9 which are elongated in the circumferential direction and are configured so as to be straight are disposed on each of the two long straight portions 20, and three are disposed on each of the two short straight portions 20. One snap-fit hook 9' which in the circumferential direction is elongate and is correspondingly arcuate is molded to each of the four arcuate portions 21.

It is a common feature of all snap-fit hooks 9, 9' that the former are assembled from a lug-type tongue portion 22 and a hook portion 23, the hook portion 23 adjoining an end of the tongue portion 22 that faces away from the cover 5. In order for the snap-fit hooks 9, 9' to be better introduced into the latching openings 11, 11', the tongue portions 22 are elastically deformable in a direction which is perpendicular to the vertical axis 8 of the container 1.

Figure 5:
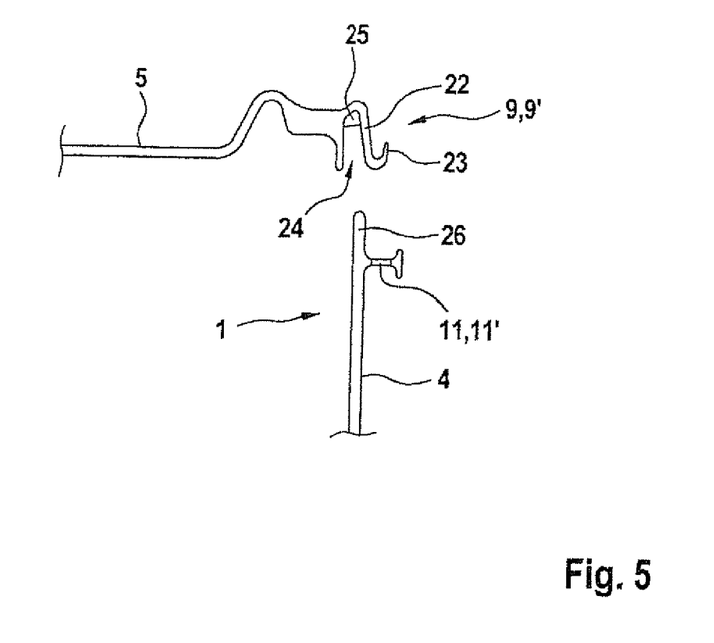
FIG. 5 shows a vertical section through the cover and the container, in the region of a snap-fit hook and of a latching opening.

FIG. 5 shows a vertical section through the container 1 and the cover 5 from FIG. 1, in the region of a snap-fit hook 9, 9' and of a latching opening 11, 11', respectively, the cover 5 and the container 1 not being joined together. The construction of the snap-fit hook 9, 9' having the tongue portion 22 thereof and the hook portion 23 thereof is clearly identifiable. It may furthermore be seen that the cover 5 is equipped in an encircling manner with a sealing groove 24 in which a seal 25 is disposed.

The container 1 has at an end that faces away from the base 3 an encircling sealing web 26 which in the present case is formed by an extension of the jacket 4 of the container 1. If and when the cover 5 and the container 1 are joined together, the sealing web 26 bears on the seal 25 in the sealing groove 24.

What is claimed is:

1. A container, comprising:
    a base;
    a jacket configured to adjoin and encircle the base, said jacket having a circumferential and outwardly projecting peripheral flange at an end that faces away from the base and defines an opening cross section to permit access to an internal volume of the container; and
    a cover configured to tightly close the opening cross section to thereby prevent access to the internal volume of the container, said cover including first snap-fit hooks distributed in circumferential spaced-apart relation about a periphery of the cover in a plane of the peripheral flange for engagement in complementing first latching openings in the peripheral flange to thereby establish a form fit that prevents a movement away from the base and parallel to a vertical axis of the container in perpendicular relation to the base,
    wherein the peripheral flange has four corner regions, each provided with a second latching opening for engagement of a second snap-fit hook of the cover, said first and second snap-fit hooks each being defined by a length in a direction of the vertical axis and a width in a direction perpendicular to the vertical axis, with the width being sized greater than the length.

2. The container of claim 1, wherein the first snap-fit hooks are elongate and the first latching openings are elongate.

3. The container of claim 1, wherein the jacket has the shape of a rounded rectangle in mutually parallel sectional planes which each run perpendicular to the vertical axis of the container, said peripheral flange having pairs of opposite straight portions in which the first latching openings are disposed, and four arcuate portions in the corner regions to correspondingly interconnect those straight portions that extend orthogonal to one another, with the second latching openings being disposed in the arcuate portions.

4. The container of claim 3, wherein the peripheral flange has the shape of a rounded rectangle.

5. The container of claim 1, wherein each of the first and second snap-fit hooks includes a tongue portion which faces the cover, and a hook portion which adjoins the tongue portion at an end facing away from the cover.

6. The container of claim 5, wherein the tongue portion is elastically deformable in a direction which is perpendicular to the vertical axis of the container.

7. The container of claim 1, wherein the first and second latching openings each have on a side which faces the vertical axis of the container a spacing from the jacket that is smaller than 5 mm.

8. The container of claim 7, wherein the spacing is smaller than 2 mm.

9. The container of claim 7, wherein the spacing is smaller than 1 mm.

10. The container of claim 1, further comprising a seal received in a circumferential sealing groove in the cover, and an encircling sealing web disposed at an end of the container facing away from the base and bearing in a sealing manner on the seal, when the cover closes the opening cross section.

11. The container of claim 10, wherein the sealing web is formed as an extension of the jacket that defines an encircling container wall.

12. The container of claim 10, wherein the sealing web has an end portion sized to extend into the sealing groove.

13. The container of claim 1, wherein the second latching opening has at least one portion configured curved or inclined in relation to both a transverse axis and a longitudinal axis of the container.

14. The container of claim 1, wherein the second latching opening has at least two straight portions extending at an inclination in relation to one another.

\* \* \* \* \*